United States Patent [19]

Soula

[11] 4,216,170
[45] Aug. 5, 1980

[54] TRIS(5-AMINO-3-THIA-PENTYL)AMINE AND METHOD OF PREPARING SAME

[75] Inventor: Gerard Soula, Meyzieu, France

[73] Assignee: Rhone-Poulenc Industries, Paris, France

[21] Appl. No.: 2,239

[22] Filed: Jan. 9, 1979

[30] Foreign Application Priority Data

Jan. 11, 1978 [FR] France ............................... 78 00624

[51] Int. Cl.$^2$ ............................................ C07C 87/20
[52] U.S. Cl. ............................................... 260/583 EE
[58] Field of Search ................................... 260/583 EE

[56] References Cited

U.S. PATENT DOCUMENTS

| | | | |
|---|---|---|---|
| 2,177,548 | 10/1939 | Jones | 260/583 EE X |
| 2,208,095 | 7/1940 | Esselmann et al. | 260/583 EE X |
| 2,304,623 | 12/1942 | Berchet | 260/583 EE |
| 2,777,858 | 1/1957 | Girod et al. | 260/583 EE X |
| 3,260,718 | 7/1966 | Johnson | 260/583 EE X |
| 3,362,996 | 1/1968 | Teumac | 260/583 EE |
| 3,725,481 | 4/1973 | Shim | 260/583 EE |
| 3,862,923 | 1/1975 | Shim | 260/583 EE |

OTHER PUBLICATIONS

Mason, "J. Chem. Soc.", pp. 320–322, (1947).

*Primary Examiner*—John Doll

[57] ABSTRACT

A new industrial product, tris(5-amino-3-thiapentyl)amine, which can be obtained by the action of tris(ethanethiol)amine on aziridine in a molar ratio of aziridine to tris(ethanethiol)amine of between about 3 and 3.5. The new product is useful as intermediate for the production of additives for lubricating oils.

1 Claim, No Drawings

TRIS(5-AMINO-3-THIA-PENTYL)AMINE AND METHOD OF PREPARING SAME

GENERAL DESCRIPTION OF THE INVENTION

The object of the present invention is to provide a new industrial product, tris(5-amino-3-thia-pentyl)amine, and a novel process for the preparing of said product.

The tris(5-amino-3-thia-pentyl)amine which forms the object of the present invention is a product of the following formula:

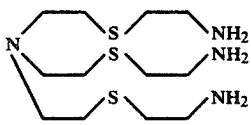

It can be prepared by the action of tris(ethanethiol)amine on aziridine in a molar ratio of aziridine to tris(ethanethiol)amine of between about 3 and 3.5, and preferably between about 3 and 3.2, at a temperature of between about 30° and 80° C., preferably between about 45° and 80° C., followed by separation of the tris(5-amino-3-thia-pentyl)amine obtained. The reaction of the process of the invention takes place in accordance with the following equation:

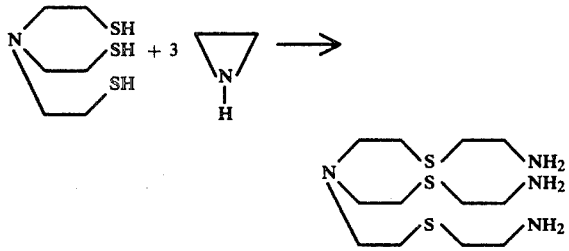

The reaction between the aziridine and the tris (ethanethiol)amine is carried out in the presence of a solvent, such as methanol, ethanol, chloroform, methylene chloride, chlorobenzene, etc. This reaction usually takes about ½ to 3 hours.

The tris(ethanethiol)amine to be used can be prepared by the action of trichlorethylamine hydrochloride on thiourea, followed by neutralization of the salt formed by a base, in accordance with the method of preparation described in *Journal Chemical Society* (1947), pages 320–322 (John Harley-Mason).

The tris (5-amino-3-thia-pentyl) amine which forms the object of the present invention can be used as intermediate for the preparation of additives for lubricating oils. Thus, when reacted with alkenyl substituted succinic acid anhydride, in which the alkenyl group contains from about 20 to 200 carbon atoms, at a temperature of between about 120° and 230° C., with the ratio of the number of equivalents of amine to alkenyl succinic anhydride comprising between about 0.4 and 0.6, the corresponding alkenyl succinimides of my copending patent application, Ser. No. 2,240, concurrently filed (Case R-2562), entitled, "Novel Alkenyl Succinimides and Process for Their Preparation," are produced. These compounds are desirable oil additives.

SPECIFIC DESCRIPTION OF THE INVENTION

The following example is given by way of illustration and is not to be considered a limitation of the scope or spirit of the invention.

EXAMPLE

Synthesis of tris(5-amino-3-thia-pentyl)amine 19.7 g., namely, 0.1 mol, of tris(thiaethanol)amine, dissolved in 250 cc. of methanol, are introduced into a threeneck 500 cc. flask provided with a mechanical agitator, a thermometer, and a dropping funnel. The mixture is heated to 45° C. 0.3 mol of aziridine (15.5 ml.) diluted in 20 cc. of methanol are then introduced over the course of 30 minutes through the dropping funnel. The mixture is then brought to the reflux temperature of the methanol (64° C.) for 3 hours, and finally, the methanol is evaporated. There are obtained 32 g. of an oily product, the chemical composition of which is:

|          | % Determined | % Theoretical |
|----------|--------------|---------------|
| Sulfur   | 29.5         | 29.4          |
| Nitrogen | 17.1         | 17.2          |
| Carbon   | 44.3         | 44.1          |
| Hydrogen | 9.15         | 9.2           |

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A novel industrial product, tris(5-amino-3-thia-pentyl)amine.

* * * * *